United States Patent
Aavula et al.

(10) Patent No.: US 9,879,017 B2
(45) Date of Patent: Jan. 30, 2018

(54) PROCESSES FOR THE PREPARATION OF AZD5363 AND INTERMEDIATE USED THEREIN

(71) Applicant: AstraZeneca AB, Sodertalje (SE)

(72) Inventors: Sanjeev Kumar Aavula, Macclesfield (GB); Vinod Kumar Chandukudlu House, Macclesfield (GB); Anil Chikkulapalli, Macclesfield (GB); Karthikeyan Chinnakalai, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 15/313,631

(22) PCT Filed: May 26, 2015

(86) PCT No.: PCT/GB2015/051525
§ 371 (c)(1),
(2) Date: Nov. 23, 2016

(87) PCT Pub. No.: WO2015/181532
PCT Pub. Date: Dec. 3, 2015

(65) Prior Publication Data
US 2017/0210745 A1    Jul. 27, 2017

Related U.S. Application Data

(60) Provisional application No. 62/003,593, filed on May 28, 2014.

(51) Int. Cl.
C07D 487/04    (2006.01)
C07D 519/00    (2006.01)

(52) U.S. Cl.
CPC ......... *C07D 487/04* (2013.01); *C07D 519/00* (2013.01)

(58) Field of Classification Search
CPC ..................... C07D 487/04; C07D 519/00
See application file for complete search history.

(56) References Cited

FOREIGN PATENT DOCUMENTS

| WO | 2009/047563 A1 | 4/2009 |
| WO | WO 2009047563 | * 4/2009 |
| WO | 2013/040044 A1 | 3/2013 |
| WO | WO 2013040044 | * 3/2013 |

OTHER PUBLICATIONS

Matt et al. (J. Med. Chem., 2013, 56(5), pp. 2059-2073).*
Matt Addie et al. Journal of Medicinal Chemistry, vol. 56, No. 5, Mar. 14, 2013, pp. 2059-2073.

* cited by examiner

*Primary Examiner* — Susanna Moore
(74) *Attorney, Agent, or Firm* — Daniel Kopp

(57) ABSTRACT

There is provided a process for the preparation of AZD5363, or a salt of AZD5363, comprising: (a) the reaction of 8-(7H-pyrrolo[2,3-d]pyrimidin-4-yl)-3-oxa-1,8-diazaspiro [4.5]decane-2,4-dione: or a salt thereof, with (S)-3-amino-3-(4-chlorophenyl)propan-1-ol, or a salt thereof, in the presence of base; and (b) either isolating AZD5363 or isolating AZD5363 as a salt. 8-(7H-pyrrolo[2,3-d]pyrimidin-4-yl)-3-oxa-1,8-diazaspiro[4.5]decane-2,4-dione is provided and is prepared by reacting 4-(alkyloxycarbonylamino)-1-(7H-pyrrolo[2,3-d]pyrimidin-4-yl)piperidine-4-carboxylic acid, or a salt thereof, with a cyclizing agent.

7 Claims, No Drawings

PROCESSES FOR THE PREPARATION OF AZD5363 AND INTERMEDIATE USED THEREIN

CROSS-REFERENCE TO RELATED APPLICATIONS

This application is a US National Stage under 35 U.S.C § 371 of International Application No. PCT/GB2015/051525 (filed 26 May 2015) which claims priority under 35 U.S.C. § 119(e) to U.S. Application No. 62/003,593 filed on 28 May 2014.

The present invention relates to chemical processes useful for the preparation of a certain pharmaceutical compound known as AZD5363. The invention also relates to an intermediate compound that has been used as part of the above-mentioned chemical processes for the improved preparation of AZD5363.

The pharmaceutical compound 'AZD5363' is alternatively known as: (S)-4-amino-N-(1-(4-chlorophenyl)-3-hydroxypropyl)-1-(7H-pyrrolo[2,3-d]pyrimidin-4-yl)piperidine-4-carboxamide, and its chemical structure is shown below:

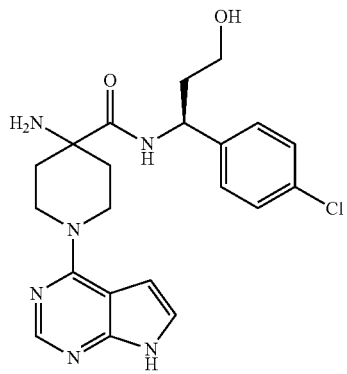 [SMILES: NC1(C(=O)N[C@@H](CCO)c2ccc(Cl)cc2)CCN(c2ncnc3[nH]ccc23)CC1]

International patent application PCT/GB2008/050925 (published as WO2009/047563) mentions AZD5363 as 'Example 9' and introduces several processes for its preparation on pages 39-42. The published methods for preparing AZD5363 were satisfactory for the preparation of relatively small quantities. However, clinical trials of AZD5363 have started since the filing of WO2009/047563 and in this context, increasing quantities of AZD5363 are now required. In our experience, the problems with the existing methods for preparing AZD5363 include low reaction yields, the formation of impurities and the need for purification steps that are not very amenable to larger-scale use, the use of chemical reagents and solvents that are disadvantageous from an environmental and/or safety and/or cost and/or convenience perspective, relatively long processing times for the overall synthesis, relatively large quantities of chemical waste per gram of AZD5363 isolated, relatively large cost per gram of AZD5363 produced, and challenges with ensuring that impurity levels in the final AZD5363 product are reliably kept to acceptable levels for use in human subjects. Accordingly there is a need for alternative routes for the preparation of AZD5363 and/or improved processing methods. One or more of the above-mentioned needs/problems have been overcome by aspects of the present invention, as described hereinafter.

Although WO2009/047563 discloses several methods for the preparation of AZD5363, our ongoing internal efforts to deliver AZD5363 for use in clinical trials has been prioritised on the route involving a BOC (t-butoxycarbonyl) deprotection as shown below:

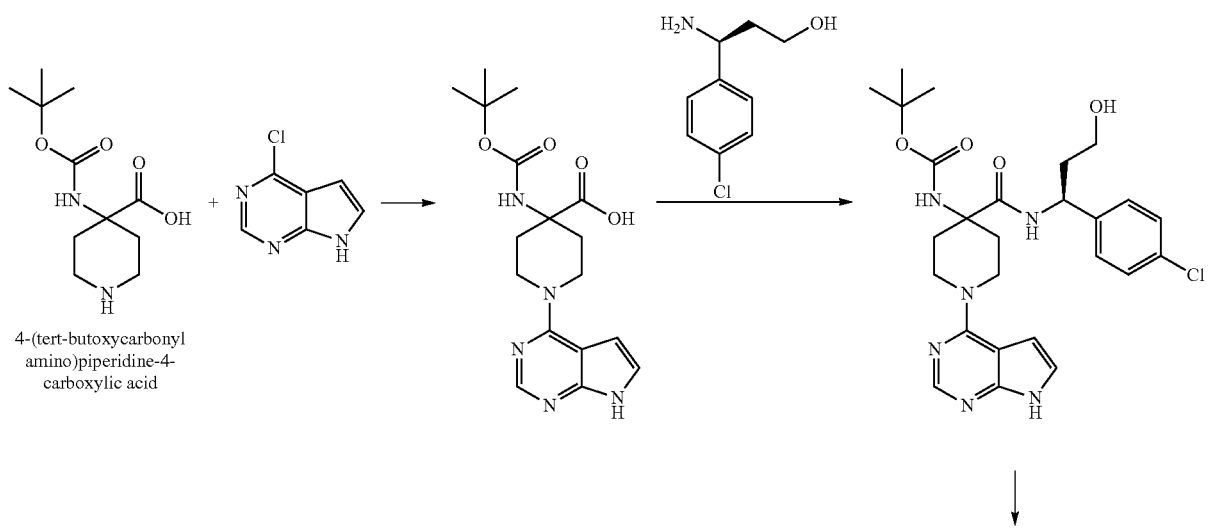

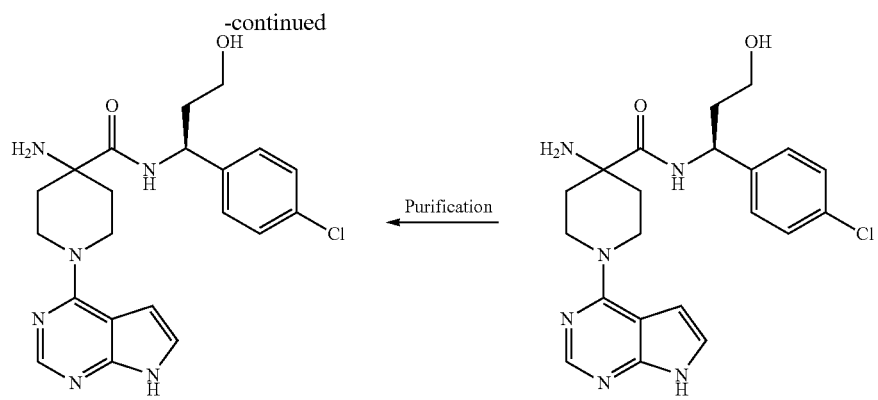

In our hands, on a large scale, this process suffers from poor throughput and low yields, and operates under high dilution and poor process mass intensity. In particular the BOC deprotection step has a tedious work-up, involving multiple solvent swaps, poor throughput and the formation of impurities, despite process development efforts having been focused on these problems. There remained a problem to produce AZD5363 in a way where the above-mentioned problems are overcome or minimized. According to the first aspect of the present invention, a solution to the problem has now been found. This solution does not merely involve a change of reaction conditions, reagents and/or solvents, but it also involves the use of an intermediate compound.

Accordingly, in the first aspect of the invention there is provided a process for the preparation of AZD5363, or a salt of AZD5363, comprising:
(a) the reaction of 8-(7H-pyrrolo[2,3-d]pyrimidin-4-yl)-3-oxa-1,8-diazaspiro[4.5]decane-2,4-dione:

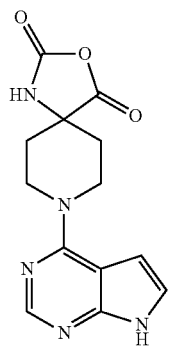 [SMILES: O=C1NC2(CCN(c3ncnc4[nH]ccc34)CC2)C(=O)O1]

or a salt thereof, with (S)-3-amino-3-(4-chlorophenyl)propan-1-ol, or a salt thereof, in the presence of base; and
(b) either isolating AZD5363 or isolating AZD5363 as a salt.

In one embodiment there is provided a process for the preparation of AZD5363, comprising the reaction of 8-(7H-pyrrolo[2,3-d]pyrimidin-4-yl)-3-oxa-1,8-diazaspiro[4.5]decane-2,4-dione or a salt thereof, with (S)-3-amino-3-(4-chlorophenyl)propan-1-ol, or a salt thereof, in the presence of base.

In a further embodiment there is provided a process for the preparation of AZD5363, comprising the reaction of 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol, in the presence of base.

In a further embodiment there is provided a process for the preparation of AZD5363, or a salt of AZD5363, comprising:
(a) the reaction of 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol, in the presence of base; and
(b) either isolating AZD5363 or isolating AZD5363 as a salt.

A person skilled in the area of chemistry will recognize that 8-(7H-pyrrolo[2,3-d]-pyrimidin-4-yl)-3-oxa-1,8-diazaspiro[4.5]decane-2,4-dione, (S)-3-amino-3-(4-chlorophenyl)-propan-1-ol and AZD5363 each possess at least one nitrogen atom that would be expected to be sufficiently basic to enable the formation of salt forms of the three aforementioned compounds. Each of these three compounds may be used, generated and/or isolated either in 'free-base' form, or in the form of a salt, but the skilled person will recognize that the use of a larger quantity of base may be appropriate in the above-mentioned process in the case where one or both of the starting materials are used in the form of a salt.

The above-mentioned process is facilitated by the use of a base. In one respect, such a base may simply be provided by the presence of one or more of 8-(7H-pyrrolo[2,3-d]-pyrimidin-4-yl)-3-oxa-1,8-diazaspiro[4.5]decane-2,4-dione in free-base form, (S)-3-amino-3-(4-chlorophenyl)propan-1-ol in free-base form and/or AZD5363 in free-base form—which may already be present in the reaction mixture, although these compounds are relatively expensive and the addition of a cheaper base provides a more efficient and/or cost effective process. Organic bases include tertiary amine bases, pyridine and substituted pyridine-based bases such as 2,6-lutidine. Examples of cheaper bases that have been used to facilitate the formation of AZD5363 in the above-mentioned process include tertiary amine bases such as triethylamine, N-methylmorpholine and diisopropylethylamine. We have shown that inorganic bases can also be used in this process. Examples of inorganic bases include hydroxides ($HO^-$), carbonates ($CO_3^{2-}$) and bicarbonates ($HCO_3^-$) of an alkali metal or alkaline earth metal (i.e. the metals found in groups 1 and 2 of the periodic table), especially the hydroxides, carbonates and bicarbonates of Li, Na, K, Rb, Cs, Mg, Ca, Sr and Ba.

In one embodiment the base is an organic base or an inorganic base.

In one embodiment the base is selected from a tertiary amine base, pyridine, a substituted pyridine base, and a hydroxide, carbonate or bicarbonate salt of an alkali metal or an alkaline earth metal.

In one embodiment the base is selected from a tertiary amine base, pyridine, a substituted pyridine base, and a hydroxide, carbonate or bicarbonate salt of Li, Na, K, Rb, Cs, Mg, Ca, Sr or Ba.

In one embodiment the base is selected from $(C_{1-6}alkyl)_3N$, N—$(C_{1-6}alkyl)$morpholine, N,N—$(C_{1-6}alkyl)_2$piperazine, N—$(C_{1-6}alkyl)$piperidine, N—$(C_{1-6}alkyl)$pyrrolidine, pyridine, 2,6-lutidine, 4-(dimethylamino)pyridine and a hydroxide, carbonate or bicarbonate salt of Li, Na, K, Rb, Cs, Mg, Ca, Sr or Ba.

In one embodiment the base is an inorganic base.

In one embodiment the base is an inorganic base selected from a hydroxide, carbonate or bicarbonate salt of an alkali metal or an alkaline earth metal.

In one embodiment the base is an inorganic base selected from a carbonate or bicarbonate salt of an alkali metal or an alkaline earth metal.

In one embodiment the base is an inorganic base selected from a hydroxide, carbonate or bicarbonate salt of Li, Na, K, Rb, Cs, Mg, Ca, Sr or Ba.

In one embodiment the base is an inorganic base selected from a carbonate or bicarbonate salt of Li, Na, K, Rb, Cs, Mg, Ca, Sr or Ba.

In one embodiment the base is an inorganic base selected from a carbonate or bicarbonate salt of Li, Na or K.

In one embodiment the base is an inorganic base selected from a bicarbonate salt of Li, Na, or K.

In one embodiment the base is potassium bicarbonate.

In this specification, "$C_{1-6}$alkyl" means a group containing from 1 to 6 carbon atoms where the only other atoms within the group are hydrogen atoms and where the group does not contain any double or triple carbon-carbon bonds. "$C_{1-6}$alkyl" includes straight chain alkyl groups, and for $C_{3-6}$alkyl groups it includes branched chain alkyl groups and alkyl groups that consist of or include a cycloalkyl group. Examples of "$C_{1-6}$alkyl" include methyl, ethyl, isopropyl, n-butyl, and cyclohexyl.

In this specification "$(C_{1-6}alkyl)_3N$" means a tertiary amine where each of the 3 substituents is a $C_{1-6}$alkyl group, as defined herein. For the avoidance of doubt, the $C_{1-6}$alkyl groups may each be the same or different when more than one such group is mentioned within a molecule such as "$(C_{1-6}alkyl)_3N$". Examples of "$(C_{1-6}alkyl)_3N$" include triethylamine, diisopropylethylamine and tricyclohexylamine.

Typically, when the 8-(7H-pyrrolo[2,3-d]pyrimidin-4-yl)-3-oxa-1,8-diazaspiro[4.5]decane-2,4-dione has been isolated as a free base, the reaction with (S)-3-amino-3-(4-chlorophenyl)propan-1-ol may be carried out in the presence of 1 to 2 mole equivalents of base. In one embodiment, the reaction of the free base of 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol may be carried out in the presence of 1.5 mole equivalents of base. Such reaction may use 1.5 mole equivalent of base, plus or minus 20%. In other embodiments such reaction may use 1.5 mole equivalent of base, plus or minus 10%.

When the 8-(7H-pyrrolo[2,3-d]pyrimidin-4-yl)-3-oxa-1,8-diazaspiro[4.5]decane-2,4-dione has been isolated as an acid salt or is prepared in situ using acidic reagents, the reaction with (S)-3-amino-3-(4-chlorophenyl)propan-1-ol may be carried out in the presence of 2 to 3 mole equivalents of base. In one embodiment, the reaction of the acid salt of 8-(7H-pyrrolo[2,3-d]pyrimidin-4-yl)-3-oxa-1,8-diazaspiro[4.5]decane-2,4-dione with (S)-3-amino-3-(4-chlorophenyl) propan-1-ol may be carried out in the presence of 2.5 mole equivalents of base. Such reaction may use 2.5 mole equivalent of base, plus or minus 20%. In other embodiments such reaction may use 2.5 mole equivalent of base, plus or minus 10%.

It is well known that chemical processes often work more effectively when the reaction components are partially or wholly dissolved into a suitable solvent. In one respect, such solvent used in the above-mentioned process may simply be provided by the presence of the base that is already included in the reaction mixture, provided that the base is a liquid under the relevant reaction conditions. The skilled person is familiar with a range of solvents that are frequently found to be suitable for organic chemistry reactions of different types. Typical solvents that may be employed for water miscible polar solvents such as dimethylformamide, dimethylacetamide, N-methylpyrollidone, dimethyl sulphoxide, sulpholane, tetrahydrofuran, acetonitrile and higher nitriles. An example of a suitable solvent is acetonitrile. Mixtures of solvents may be used, for example in one embodiment a mixture of acetonitrile and water is used. A solvent mixture including water may be preferable when an inorganic base is used as the base, as this may help ensure or encourage dissolution of the inorganic base.

In one embodiment there is provided a process for the preparation of AZD5363, or a salt of AZD5363, comprising: (a) the reaction of 8-(7H-pyrrolo[2,3-d]pyrimidin-4-yl)-3-oxa-1,8-diazaspiro[4.5]decane-2,4-dione:

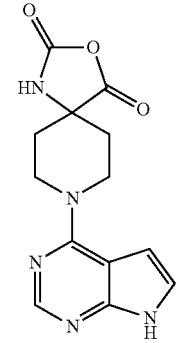 [SMILES: O=C1NC2(CCN(c3ncnc4[nH]ccc34)CC2)C(=O)O1]

or a salt thereof, with (S)-3-amino-3-(4-chlorophenyl)propan-1-ol, or a salt thereof, in the presence of base and solvent; and
(b) either isolating AZD5363 or isolating AZD5363 as a salt.

The processes described herein may provide AZD5363 as a free base, or as a salt if desired. The processes for preparing such a salt are well known and may preferably involve the mixture of the amine compound (e.g. AZD5363) with an appropriate quantity (e.g. 1:1 molar ratio) of an organic or inorganic acid, in a suitable solvent. The resulting salt may sometimes precipitate or crystallize from the solution and in these cases it may be isolated by filtration. The resulting salt may alternatively be isolated by evaporation of the solvent.

In our hands, the process for producing AZD5363 from 8-(7H-pyrrolo[2,3-d]-pyrimidin-4-yl)-3-oxa-1,8-diazaspiro[4.5]decane-2,4-dione can sometimes proceed less cleanly and/or less completely than desired, depending on the conditions used. It could be speculated that the anhydride functional group within 8-(7H-pyrrolo[2,3-d]-pyrimidin-4-yl)-3-oxa-1,8-diazaspiro[4.5]decane-2,4-dione might be susceptible to side reactions, for example reactions with nucleophiles such as hydroxide. Any such reaction could be expected to lead to impurities and lower yields of AZD5363 and might encourage the use of strictly anhydrous solvents and conditions. However, surprisingly, we have found that the use of water as a co-solvent, in combination with an inorganic base is actually very beneficial for achieving low levels of impurities, improving the reaction rate and helping to drive the reaction to completion.

Accordingly, in this aspect of the invention there is provided a process for the preparation of AZD5363, or a salt of AZD5363, comprising:
(a) the reaction of 8-(7H-pyrrolo[2,3-d]pyrimidin-4-yl)-3-oxa-1,8-diazaspiro[4.5]decane-2,4-dione or a salt thereof, with (S)-3-amino-3-(4-chlorophenyl)propan-1-ol, or a salt thereof, in the presence of base and solvent; and
(b) either isolating AZD5363 or isolating AZD5363 as a salt; wherein the base is one or more inorganic bases and the solvent is a mixture of water together with one or more organic solvents wherein the water comprises between 5% and 50% v/v of the total solvent.

In one embodiment there is provided a process for the preparation of AZD5363, comprising the reaction of 8-(7H-pyrrolo[2,3-d]pyrimidin-4-yl)-3-oxa-1,8-diazaspiro[4.5]decane-2,4-dione, or a salt thereof, with (S)-3-amino-3-(4-chlorophenyl)propan-1-ol, or a salt thereof, in the presence of base and solvent; wherein the base is one or more inorganic bases and the solvent is a mixture of water together with one or more organic solvents wherein the water comprises between 5% and 30% v/v of the total solvent.

In a further embodiment there is provided a process for the preparation of AZD5363, comprising the reaction of 8-(7H-pyrrolo[2,3-d]pyrimidin-4-yl)-3-oxa-1,8-diazaspiro[4.5]decane-2,4-dione, or a salt thereof, with (S)-3-amino-3-(4-chlorophenyl)propan-1-ol, or a salt thereof, in the presence of base and solvent; wherein the base is one or more inorganic bases and the solvent is a mixture of water together with one or more organic solvents wherein the water comprises between 7.5% and 22.5% v/v of the total solvent.

In a further embodiment there is provided a process for the preparation of AZD5363, or a salt of AZD5363, comprising:
(a) the reaction of 8-(7H-pyrrolo[2,3-d]pyrimidin-4-yl)-3-oxa-1,8-diazaspiro[4.5]decane-2,4-dione, or a salt thereof, with (S)-3-amino-3-(4-chlorophenyl)propan-1-ol, or a salt thereof, in the presence of base and solvent; and
(b) either isolating AZD5363 or isolating AZD5363 as a salt; wherein the base is one or more inorganic bases and the solvent is a mixture of water together with one or more organic solvents wherein the water comprises between 10% and 20% v/v of the total solvent.

8-(7H-Pyrrolo[2,3-d]pyrimidin-4-yl)-3-oxa-1,8-diazaspiro[4.5]decane-2,4-dione may be prepared and isolated prior to use in the reaction with (S)-3-amino-3-(4-chlorophenyl)propan-1-ol. Alternatively, 8-(7H-pyrrolo[2,3-d]pyrimidin-4-yl)-3-oxa-1,8-diazaspiro[4.5]decane-2,4-dione may be prepared in situ and used directly without isolation.

In one embodiment, there is provided a process for the preparation of AZD5363, or a salt of AZD5363, comprising:
(a) the reaction of compound of 4-(alkyloxycarbonylamino)-1-(7H-pyrrolo[2,3-d]pyrimidin-4-yl)piperidine-4-carboxylic acid, or a salt thereof, with a cyclising agent to give 8-(7H-pyrrolo[2,3-d]pyrimidin-4-yl)-3-oxa-1,8-diazaspiro[4.5]decane-2,4-dione;
(b) optionally isolating the 8-(7H-pyrrolo[2,3-d]pyrimidin-4-yl)-3-oxa-1,8-diazaspiro[4.5]decane-2,4-dione;
(c) the reaction of 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol, or a salt thereof, in the presence of base; and
(d) either isolating AZD5363 or isolating AZD5363 as a salt.

In one embodiment, there is provided a process for the preparation of AZD5363, or a salt of AZD5363, comprising:
(a) the reaction of compound of 4-(alkyloxycarbonylamino)-1-(7H-pyrrolo[2,3-d]pyrimidin-4-yl)piperidine-4-carboxylic acid, or a salt thereof, with a cyclising agent to give 8-(7H-pyrrolo[2,3-d]pyrimidin-4-yl)-3-oxa-1,8-diazaspiro[4.5]decane-2,4-dione;
(b) reacting the 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol, or a salt thereof, in the presence of base; and then
(c) either isolating AZD5363 or isolating AZD5363 as a salt.

In one embodiment, there is provided a process for the preparation of AZD5363, or a salt of AZD5363, comprising:
(a) the reaction of compound of 4-(alkyloxycarbonylamino)-1-(7H-pyrrolo[2,3-d]pyrimidin-4-yl)piperidine-4-carboxylic acid, or a salt thereof, with a cyclising agent in the presence of a first solvent to give 8-(7H-pyrrolo[2,3-d]pyrimidin-4-yl)-3-oxa-1,8-diazaspiro[4.5]decane-2,4-dione;
(b) optionally isolating the 8-(7H-pyrrolo[2,3-d]pyrimidin-4-yl)-3-oxa-1,8-diazaspiro[4.5]decane-2,4-dione;
(c) the reaction of 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol, or a salt thereof, in the presence of base and second solvent; and
(d) either isolating AZD5363 or isolating AZD5363 as a salt.

In one embodiment, there is provided a process for the preparation of AZD5363, or a salt of AZD5363, comprising:
(a) the reaction of compound of 4-(alkyloxycarbonylamino)-1-(7H-pyrrolo[2,3-d]pyrimidin-4-yl)piperidine-4-carboxylic acid, or a salt thereof, with a cyclising agent in the presence of a first solvent to give 8-(7H-pyrrolo[2,3-d]pyrimidin-4-yl)-3-oxa-1,8-diazaspiro[4.5]decane-2,4-dione;
(b) optionally isolating the 8-(7H-pyrrolo[2,3-d]pyrimidin-4-yl)-3-oxa-1,8-diazaspiro[4.5]decane-2,4-dione;
(c) the reaction of 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol, or a salt thereof, in the presence of base and second solvent; and
(d) either isolating AZD5363 or isolating AZD5363 as a salt; wherein the base is one or more inorganic bases and the second solvent is a mixture of water together with one or more organic solvents wherein the water comprises between 5% and 50% v/v of the total solvent.

In a further embodiment, there is provided a process for the preparation of AZD5363, or a salt of AZD5363, comprising:
(a) the reaction of compound of 4-(t-butyloxycarbonylamino)-1-(7H-pyrrolo[2,3-d]pyrimidin-4-yl)piperidine-4-carboxylic acid, or a salt thereof, with a cyclising agent in the presence of a first solvent to give 8-(7H-pyrrolo[2,3-d]pyrimidin-4-yl)-3-oxa-1,8-diazaspiro[4.5]decane-2,4-dione;
(b) optionally isolating the 8-(7H-pyrrolo[2,3-d]pyrimidin-4-yl)-3-oxa-1,8-diazaspiro[4.5]decane-2,4-dione;
(c) the reaction of 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol, or a salt thereof, in the presence of base and second solvent; and
(d) either isolating AZD5363 or isolating AZD5363 as a salt; wherein the base is one or more inorganic bases and the second solvent is a mixture of water together with one or more organic solvents wherein the water comprises between 10% and 20% v/v of the total solvent.

In one embodiment the 4-(alkyloxycarbonylamino)-1-(7H-pyrrolo[2,3-d]pyrimidin-4-yl)piperidine-4-carboxylic acid is a 4-($C_{1-6}$-alkyloxycarbonylamino)-1-(7H-pyrrolo[2,3-d]pyrimidin-4-yl)piperidine-4-carboxylic acid.

In one embodiment the 4-(alkyloxycarbonylamino)-1-(7H-pyrrolo[2,3-d]pyrimidin-4-yl)piperidine-4-carboxylic acid is a 4-($C_4$-alkyloxycarbonylamino)-1-(7H-pyrrolo[2,3-d]pyrimidin-4-yl)piperidine-4-carboxylic acid.

In one embodiment the 4-(alkyloxycarbonylamino)-1-(7H-pyrrolo[2,3-d]pyrimidin-4-yl)piperidine-4-carboxylic acid is a 4-(t-butyloxycarbonylamino)-1-(7H-pyrrolo[2,3-d]pyrimidin-4-yl)piperidine-4-carboxylic acid.

The first and second solvent may be the same of different and are selected from the solvents listed above.

In one embodiment the first and second solvents are the same.

In one embodiment, where the second solvent is a mixture of more than one solvent, the first solvent comprises at least one of the solvents present in the mixture of solvents.

In one embodiment, the first solvent is acetonitrile.

In one embodiment, the second solvent is acetonitrile and water.

In one embodiment, the first solvent is acetonitrile and the second solvent is acetonitrile and water.

When the second solvent is acetonitrile and water, in one embodiment the water comprises between 5% and 50% v/v of the total solvent.

When the second solvent is acetonitrile and water, in another embodiment the water comprises between 5% and 30% v/v of the total solvent.

When the second solvent is acetonitrile and water, in a further embodiment the water comprises between 7.5% and 22.5% v/v of the total solvent.

When the second solvent is acetonitrile and water, in a further embodiment the water comprises between 10% and 20% v/v of the total solvent.

Cyclising agents that may be employed in the reaction of 4-(alkyloxycarbonylamino)-1-(7H-pyrrolo[2,3-d]pyrimidin-4-yl)piperidine-4-carboxylic acid include acid chlorides, acid anhydrides, phosgene equivalents, carbodimides and halotriazines.

Acid chlorides include thionyl chloride, oxayly chloride, pivolyl chloride, trichloroacetyl chloride, trifluoroacetyl chloride.

Acid anhydrides include trichloroacetic anhydride, trifluoroacetic anhydride.

Phosgene equivalents include phosgene, diphosgene and triphosgene.

Carbodiimides and halotriazines include N-(3-dimethylaminopropyl)-N'-ethylcarbodiimide, typically as the hydrochloride salt (EDC.HCl) and 2-chloro-4, 6-dimethoxy-1, 3, 5-triazine (CDMT)

In one embodiment, the cyclising agent is trifluoroacetic anhydride or trichloroacetyl chloride.

In one embodiment, the cyclising agent is trifluoroacetic anhydride.

In one embodiment, the cyclising agent is trichloroacetyl chloride.

In one embodiment, 1.0 to 1.5 mole equivalents of cyclising agent is used (with respect to the substrate that is being cyclised eg 4-(t-butyloxycarbonylamino)-1-(7H-pyrrolo[2, 3-d]pyrimidin-4-yl)piperidine-4-carboxylic acid). In a further embodiment 1.3 mole equivalents, plus or minus 10%, cyclising agent is used.

In a further embodiment, there is provided a process for the preparation of AZD5363, or a salt of AZD5363, comprising:

(a) the reaction of compound of 4-(t-butyloxycarbonylamino)-1-(7H-pyrrolo[2,3-d]pyrimidin-4-yl)piperidine-4-carboxylic acid with a cyclising agent in the presence of a first solvent to give 8-(7H-pyrrolo[2,3-d]pyrimidin-4-yl)-3-oxa-1,8-diazaspiro[4.5]decane-2,4-dione wherein the cyclising agent is trifluoroacetic anhydride and the first solvent is acetonitrile;

(b) optionally isolating the 8-(7H-pyrrolo[2,3-d]pyrimidin-4-yl)-3-oxa-1,8-diazaspiro[4.5]decane-2,4-dione; and then (c) reacting the 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol, in the presence of base and second solvent; and (d) either isolating AZD5363 or isolating AZD5363 as a salt;

wherein the base is potassium bicarbonate and the second solvent is a mixture of acetonitrile and water wherein the water comprises between 10% and 20% v/v of the total solvent.

In a further aspect of the invention there is provided 8-(7H-pyrrolo[2,3-d]pyrimidin-4-yl)-3-oxa-1,8-diazaspiro[4.5]decane-2,4-dione, or a salt thereof.

In a further aspect of the invention there is provided AZD5363 or a salt thereof, obtainable by any of the processes described herein.

In a further aspect of the invention there is provided AZD5363 or a salt thereof, obtained by any of the processes described herein.

In our hands the new methods described to prepare AZD5363 shorten the synthesis to 3 steps starting from 4-(tert-butoxycarbonylamino)piperidine-4-carboxylic acid. The new methods offer a better isolation procedure for AZD5363. The new methods offer the ability to eliminate solvents that are subject to regulatory restrictions. The new methods have improved environmental profiles, in particular the new methods reduce the amount and number of solvents deployed. The new methods increase overall yields. In addition, these factors together lead to an overall cost benefit.

It is understood that AZD5363 prepared by the processes described herein may be used to provide formulations such as tablets for use as medicaments for the treatment of cancer. Suitable formulations and treatment uses for the medicaments so prepared are described in WO2009/047563.

GENERAL EXPERIMENTAL

The invention will now be further explained by reference to the following illustrative examples.

The following abbreviations are used herein or within the following illustrative examples:—

HPLC High Performance Liquid Chromatography
PDA Photodiode Array Detector
ACN Acetonitrile
DMSO dimethylsulfoxide
TFA trifluoroacetic acid
The chemical names were generated by software from ACD labs Version 12.0

Unless stated otherwise, starting materials were commercially available. All solvents and commercial reagents were of laboratory grade and were used as received.

Scheme
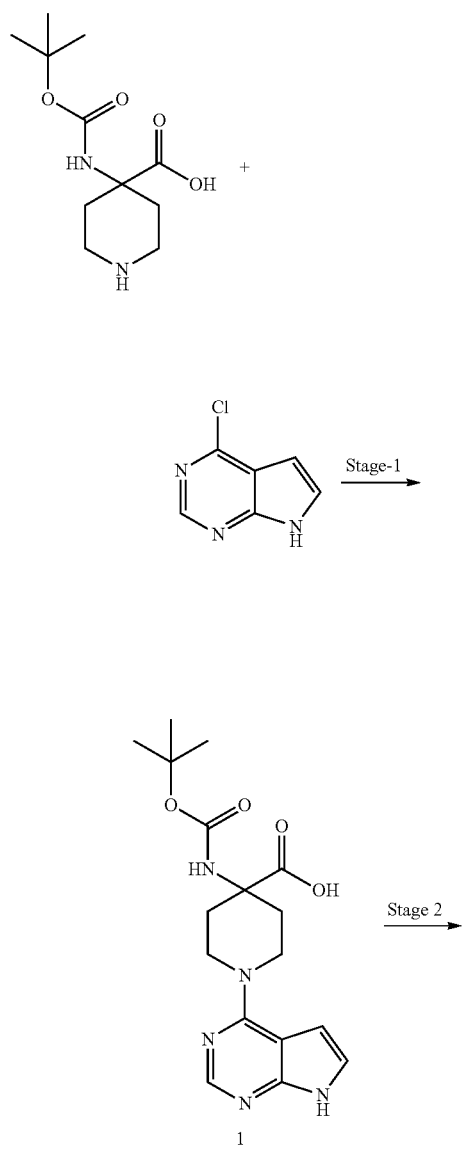
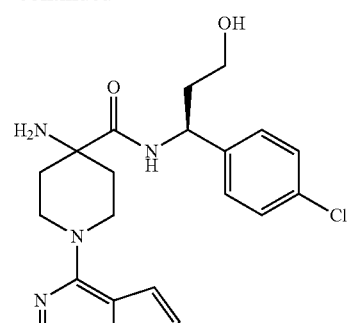
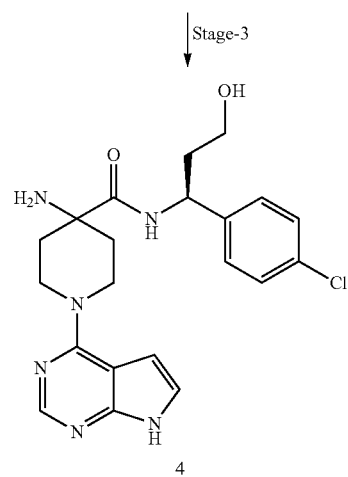
Stage 1: Water, Acetonitrile, NaOH, 2-MethylTHF.
Stage 2: Acetonitrile, Trifluoroacetic Anhydride, Water, KHCO₃, NaOH, Isopropanol
Stage 3: Ethanol
Example 1. Preparation of 4-amino-N-[1S)-1-(4-chlorophenyl)-3-hydroxy-propyl]-1-(7H-pyrrolo[2,3-d]pyrimidin-4-yl)piperidine-4-carboxamide (Leuchs Anhydride Non Isolated)
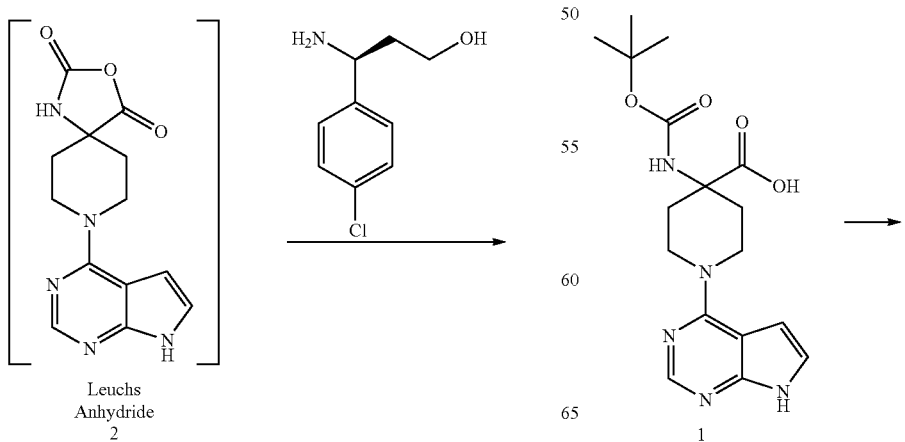

-continued

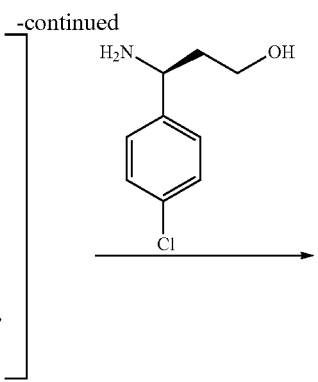

Chromatographic Conditions:

Chromatographic separation was achieved on Agilent LC systems equipped with PDA detectors using Atlantis T3 column and a mixture of Water:ACN:TFA as an eluent.

$^1$H NMR—(400.13 MHz, DMSO-$d_6$) δ: 11.68 (1H, s), 8.48 (1H, d), 8.13 (1H, s), 7.37-7.31 (4H, m), 7.16-7.15 (1H, m), 6.57 (1H, m), 4.88 (1H, d), 4.53 (1H, t), 4.41-4.34 (2H, m), 3.59-3.50 (2H, m), 3.40-3.35 (2H, m), 2.17 (2H, s), 2.02-1.80 (4H, m), 1.47-1.39 (2H, m).

Example 2: Preparation of 4-amino-N-[(1S)-1-(4-chlorophenyl)-3-hydroxy-propyl]-1-(7H-pyrrolo[2,3-d]pyrimidin-4-yl)piperidine-4-carboxamide (without Isolating Leuchs Anhydride)

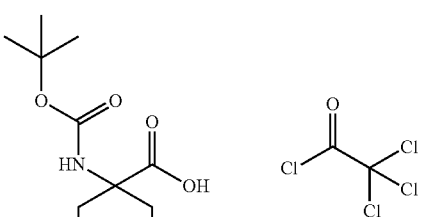

To a stirred suspension of 4-(t-butoxycarbonylamino)-1-(7H-pyrrolo[2,3-d]pyrimidin-4-yl)piperidine-4-carboxylic acid (1, 1.0 mol.eq, 46.0 g) in acetonitrile (10.0 rel.vols, 460.0 mL) was slowly added trifluoroacetic anhydride (1.3 mol.eq, 23.26 mL) at 10 to 15° C. over a period of 15 to 20 minutes under nitrogen atmosphere. The mixture was stirred for 90 minutes at 25° C. Then potassium bicarbonate (2.5 mol.eq, 31.86 g) and acetonitrile (3.5 rel.vol, 161.0 mL) were added and the reaction mixture stirred for 5-10 mins at 25° C. Then (3S)-3-amino-3-(4-chlorophenyl)propan-1-ol (1.2 mol.eq, 31.47 g) and water (1.5 rel.vols, 69.0 mL) were added and the reaction mixture stirred at 25° C. for 8-10 hrs. Water (5.0 rel.vols, 230.0 mL) was charged to the reaction mixture and then the mixture was distilled at 50-55° C. under reduced pressure, until the residual volume reached 5-6 rel.vols, 230.0 mL. Isopropyl alcohol (4.0 rel.vols, 184.0 mL) was added to the concentrated reaction mass and the pH adjusted to pH ~12.0-12.5 using 10% aqueous sodium hydroxide solution (0.7 rel.vols, 32.2 mL) at 25° C. The reaction contents were then heated to 55-60° C. and pH re-adjusted to pH~12.0-12.5 using 10% aqueous sodium hydroxide solution (0.6 rel.vol, 27.6 mL) at 55-60° C. The mixture was stirred for 90 mins and water (10.0 rel.vols, 460.0 mL) was added at 55-60° C. The mixture was then cooled slowly to 35° C. over a period of 60-90 mins. An aliquot of purified AZD5363 (0.005 mol. Eq, 0.27 g) was added at 35° C. in order to seed crystallization and the reaction contents were stirred for 30 mins. Water (15 rel.vols) was added and stirred for 16-18 hrs at 22-25° C. The mixture was then filtered, and the precipitated solid was isolated and dried at 60° C. under vacuum to give desired 4-amino-N-[(1S)-1-(4-chlorophenyl)-3-hydroxy-propyl]-1-(7H-pyrrolo[2,3-d]pyrimidin-4-yl)-piperidine-4-carboxamide 3 as an white to off white solid with 84.19% yield and Purity: 99% by HPLC area.

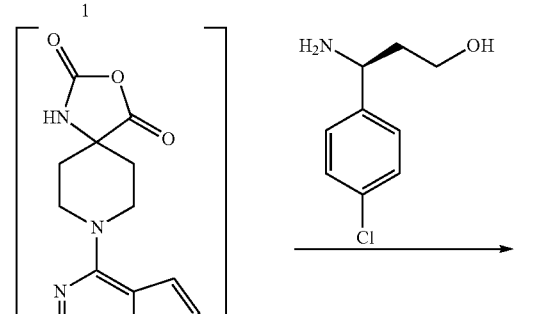

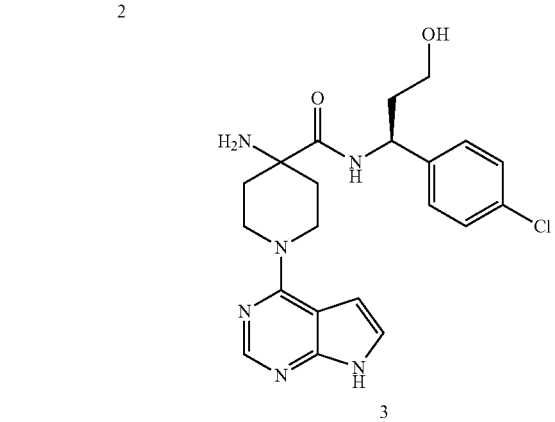

To a stirred suspension of 4-(t-butoxycarbonylamino)-1-(7H-pyrrolo[2,3-d]pyrimidin-4-yl)piperidine-4-carboxylic acid (1, 46.0 g, 127.2 mmole) in acetonitrile (10.0 rel.vols, 460.0 mL) added slowly 2,2,2-trichloroacetyl chloride (1.5 mol.eq, 21.42 mL) at 10 to 15° C. over a period of 15 to 20 minutes under nitrogen atmosphere. The reaction contents were stirred for 90 minutes at 25° C. Potassium bicarbonate (2.5 mol.eq, 31.86 g) and acetonitrile (3.5 rel.vol, 161.0 mL) was added to the reaction contents and stirred for 5-10 mins at 25° C., then (3S)-3-amino-3-(4-chlorophenyl)propan-1-ol (1.2 mol.eq, 31.47 g) was added and then water (1.5 rel.vols, 69.0 mL) was added and the reaction mixture stirred at 25° C. for 10 hrs. Water (5.0 rel.vols, 230.0 mL) was charged to the reaction mixture and the reaction mass distilled at 50-55° C. under reduced pressure, until the residual volume reaches to 5-6 rel.vol. Isopropyl alcohol (4.0 rel.vols, 184.0 mL) was added to the concentrated reaction mass and the pH adjusted to pH~12.0-12.5 using 10% w/v sodium hydroxide solution (0.7 rel.vols, 32.2 mL) at 25° C. The reaction contents were heated to 55-60° C. and the pH re-adjusted to pH~12.0-12.5 using 10% w/v sodium hydroxide solution (0.6 rel.vol, 27.6 mL) at 55-60° C. The mixture was stirred for 90 mins and water (10.0 rel.vols, 460.0 mL) was added at 55-60° C. The reaction mixture was cooled slowly to 22-25° C. over the period of 60-90 mins. Water (10.0 rel.vols, 460.0 mL) was added and stirred for 18-20 hrs at 22-25° C. The mixture was filtered and the precipitated solid was isolated and dried at 60° C. under vacuum to give desired 4-amino-N-[(1S)-1-(4-chlorophenyl)-3-hydroxy-propyl]-1-(7H-pyrrolo[2,3-d]pyrimidin-4-yl)piperidine-4-carboxamide 3 as an off white solid, 49.0 g (84.19%), Purity (98.24% by HPLC area).

Chromatographic Conditions:

Chromatographic separation was achieved on Agilent LC systems equipped with PDA detectors using Atlantis T3 column and a mixture of Water:ACN:TFA as an eluent.

$^1$H NMR—(400.13 MHz, DMSO-$d_6$) δ: 11.68 (1H, s), 8.48 (1H, d), 8.13 (1H, s), 7.37-7.31 (4H, m), 7.16-7.15 (1H, m), 6.57 (1H, m), 4.88 (1H, d), 4.53 (1H, t), 4.41-4.34 (2H, m), 3.59-3.50 (2H, m), 3.40-3.35 (2H, m), 2.17 (2H, s), 2.02-1.80 (4H, m), 1.47-1.39 (2H, m).

Example 3. Preparation of 4-amino-N-[(1S)-1-(4-chlorophenyl)-3-hydroxy-propyl]-1-(7H-pyrrolo[2,3-d]pyrimidin-4-yl)piperidine-4-carboxamide (3) (from Isolated Leuchs Anhydride)

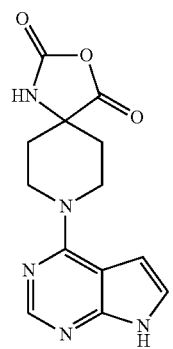

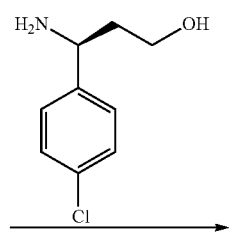

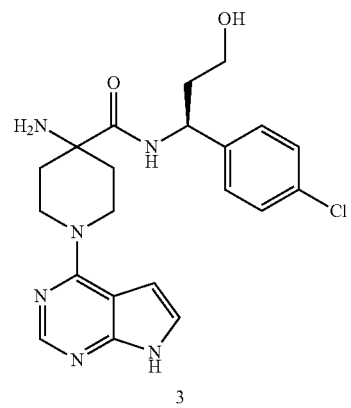

To a stirred suspension of 8-(7H-pyrrolo[2,3-d]pyrimidin-4-yl)-2-oxa-4,8-diazaspiro [4.5]-decane-1,3-dione free base (2, 3.0 g, 10.45 mmole) in acetonitrile (10.0 rel.vols, 30.0 mL) was added potassium bicarbonate (2.5 mol.eq, 2.64 g, 26.36 mmole), (3S)-3-amino-3-(4-chlorophenyl)propan-1-ol (1.2 mol.eq, 2.61 g, 12.67 mmole), water (1.5 rel.vols, 4.5 mL) and acetonitrile (3.5 rel.vol, 10.5 mL). The reaction mixture stirred at 25° C. for 10 hrs. Water (5.0 rel.vols, 15.0 mL) was charged to the reaction mixture and the reaction mass distilled at 50-55° C. under reduced pressure, until the residual volume reaches to 5-6 rel.vols. Isopropyl alcohol (4.0 rel.vols, 12.0 mL) was added to the concentrated reaction mass and the pH adjusted to pH ~12.0-12.5 using 10% w/v sodium hydroxide solution (0.6 rel.vols, 1.8 mL) at 25° C. The reaction mixture was heated to 55-60° C. and the pH re-adjusted to pH~12.0-12.5 using 10% w/v sodium hydroxide solution (0.6 rel.vol, 1.8 mL) at 55-60° C. The mixture was stirred for 90 mins and water (10.0 rel.vols, 30.0 mL) was added at 55-60° C. The reaction mixture was cooled slowly to 22-25° C. over a period of 60-90 mins. Water (10.0 rel.vols, 30.0 mL) was added and stirred for 18-20 hrs at 22-25° C. The mixture was filtered and the precipitated solid isolated and then dried at 60° C. under vacuum to give desired 4-amino-N-[(1S)-1-(4-chlorophenyl)-3-hydroxy-propyl]-1-(7H-pyrrolo[2,3-d]pyrimidin-4-yl)piperidine-4-carboxamide 3 as an off white solid, 3.8 g (80.0%), Purity (99.0% by HPLC area).

Chromatographic Conditions:

Chromatographic separation was achieved on Agilent LC systems equipped with PDA detectors using Atlantis T3 column and a mixture of Water:ACN:TFA as an eluent.

$^1$H NMR—(400.13 MHz, DMSO-$d_6$) δ: 11.68 (1H, s), 8.48 (1H, d), 8.13 (1H, s), 7.37-7.31 (4H, m), 7.16-7.15 (1H, m), 6.57 (1H, m), 4.88 (1H, d), 4.53 (1H, t), 4.41-4.34 (2H, m), 3.59-3.50 (2H, m), 3.40-3.35 (2H, m), 2.17 (2H, s), 2.02-1.80 (4H, m), 1.47-1.39 (2H, m).

Preparation of 8-(7H-pyrrolo[2,3-d]pyrimidin-4-yl)-2-oxa-4,8-diazaspiro[4.5]decane-1,3-dione (Leuchs Anhydride Free Base)

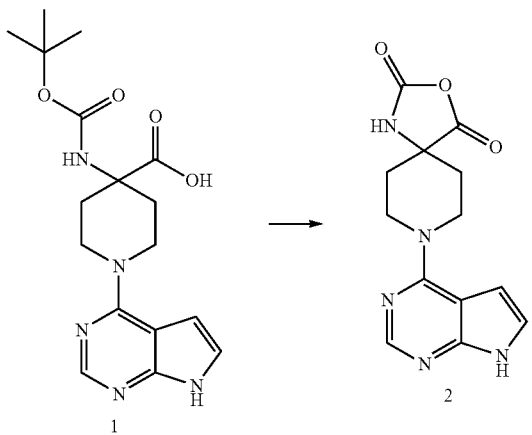 [SMILES: CC(C)(C)OC(=O)NC1(C(=O)O)CCN(c2ncnc3[nH]ccc23)CC1 ; O=C1NC2(CCN(c3ncnc4[nH]ccc34)CC2)C(=O)O1]

To a stirred solution of 2-chloro-4,6-dimethoxy-1,3,5-triazine (1.3 mol.eq, 3.04 g) in acetonitrile (10.0 rel.vols, 47.6 mL) was added N-methylmorpholine (1.3 mol.eq, 1.9 mL) at 22-25° C. The reaction contents were stirred for 10 mins at 22-25° C. 4-(tert-butoxycarbonylamino)-1-(7H-pyrrolo[2,3-d]pyrimidin-4-yl)piperidine-4-carboxylic acid (1, 4.76 g, 1.0 mol.eq) was added and the reaction mixture heated to 45-50° C. The mixture was stirred for 6-8 hrs at 45-50° C. and then cooled to 22-25° C. The mixture was filtered and the precipitated solid isolated to give 8-(7H-pyrrolo[2,3-d]pyrimidin-4-yl)-2-oxa-4,8-diazaspiro[4.5]decane-1,3-dione (2) as a solid; 4.4 g (84.0%), Purity=96.5% by HPLC area.

Chromatographic Conditions:
Chromatographic separation was achieved on Agilent LC systems equipped with PDA detectors using Atlantis T3 column and a mixture of Water:ACN:TFA as an eluent.

$^1$H NMR—(DMSO-$d_6$) δ: 11.79 (s, 1H), 9.68 (s, 1H), 8.19 (s, 1H), 7.23 (s, 1H), 6.63 (s, 1H), 4.37-4.33 (m, 2H), 3.70-3.67 (m, 2H), 2.00-1.92 (m, 4H).

$^{13}$C NMR—(DMSO-$d_6$): 171.7, 154.9, 150.9, 149.5, 149.4, 120.6, 101.2, 99.5, 59.7, 40.1, 31.4.

Alternate Preparation of 8-(7H-pyrrolo[2,3-d]pyrimidin-4-yl)-2-oxa-4,8-diazaspiro [4.5]-decane-1,3-dione (Leuchs Anhydride Trifluoroacetate Salt) (2)

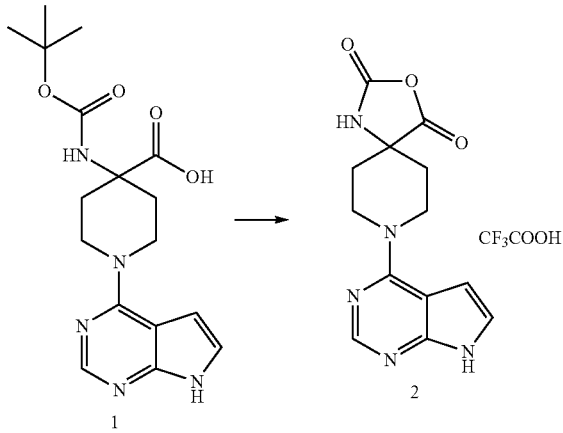 [SMILES: CC(C)(C)OC(=O)NC1(C(=O)O)CCN(c2ncnc3[nH]ccc23)CC1 ; O=C1NC2(CCN(c3ncnc4[nH]ccc34)CC2)C(=O)O1 ; "CF3COOH"]

To a stirred suspension of 4-(tert-butoxycarbonylamino)-1-(7H-pyrrolo[2,3-d]pyrimidin-4-yl)piperidine-4-carboxylic acid (1, 1.0 mol.eq, 46.0 g) in acetonitrile (10.0 rel.vols, 460.0 mL) was added slowly trifluoroacetic anhydride (1.3 mol.eq, 23.26 mL) at 10 to 15° C. over a period of 15 to 20 minutes under nitrogen atmosphere. The reaction mixture was stirred for 90 minutes at 25° C. The mixture was filtered and the precipitated solid isolated to give 8-(7H-pyrrolo[2,3-d]pyrimidin-4-yl)-2-oxa-4,8-diazaspiro[4.5]decane-1,3-dione as the trifluoroacetate salt (2) as a solid with 80% isolated yield, Purity=97% by HPLC area.

Chromatographic Conditions:
Chromatographic separation was achieved on Agilent LC systems equipped with PDA detectors using Atlantis T3 column and a mixture of Water:ACN:TFA as an eluent.

$^1$H NMR (DMSO-$d_6$) δ: 12.52 (s, 1H), 9.73 (s, 1H), 8.35 (s, 1H), 7.39 (s, 1H), 6.85 (d, 1H), 4.36 (m, 2H), 3.79 (m, 2H), 2.25-1.93 (m, 4H)

$^{13}$C NMR—(DMSO-d6): 172.6, 159.1, 158.8, 158.5, 158.1, 153.6, 150.6, 147.3, 145.6, 123.4, 120.6, 117.7, 114.7, 111.8, 120.6, 102.0, 60.4, 42.3, 32.5.

The invention claimed is:

1. A process for the preparation of AZD5363, or a salt of AZD5363, comprising:
   (a) the reaction of 8-(7H-pyrrolo[2,3-d]pyrimidin-4-yl)-3-oxa-1,8-diazaspiro[4.5]decane-2,4-dione:

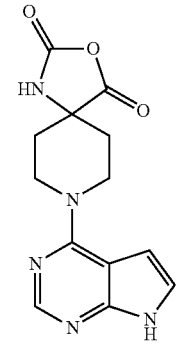 [SMILES: O=C1NC2(CCN(c3ncnc4[nH]ccc34)CC2)C(=O)O1]

or a salt thereof, with (S)-3-amino-3-(4-chlorophenyl)propan-1-ol, or a salt thereof, in the presence of base; and
   (b) either isolating AZD5363 or isolating AZD5363 as a salt.

2. A process for the preparation of AZD5363, or a salt of AZD5363, comprising:
   (a) the reaction of compound of 4-(alkyloxycarbonylamino)-1-(7H-pyrrolo[2,3-d]pyrimidin-4-yl)piperidine-4-carboxylic acid, or a salt thereof, with a cyclizing agent to give 8-(7H-pyrrolo[2,3-d]pyrimidin-4-yl)-3-oxa-1,8-diazaspiro[4.5]decane-2,4-dione;
   (b) reacting the 8-(7H-pyrrolo[2,3-d]pyrimidin-4-yl)-3-oxa-1,8-diazaspiro[4.5]decane-2,4-dione with (S)-3-amino-3-(4-chlorophenyl)propan-1-ol, or a salt thereof, in the presence of base; and then
   (c) either isolating AZD5363 or isolating AZD5363 as a salt.

3. A process according to claim 1 wherein the base is one or more inorganic bases.

4. A process according to claim 3 where the base is potassium bicarbonate.

5. A process according to claim 1 wherein the reaction reaction of 8-(7H-pyrrolo[2,3-d]pyrimidin-4-yl)-3-oxa-1,8- diazaspiro[4.5]decane-2,4-dione, or a salt thereof, with (S)-3-amino-3-(4-chlorophenyl)propan-1-ol is in the presence of a solvent.

6. A process according to claim 5 wherein the solvent is a mixture of acetonitrile and water.

7. 8-(7H-pyrrolo[2,3-d]pyrimidin-4-yl)-3-oxa-1,8-diazaspiro[4.5]decane-2,4-dione, or a salt thereof.

\* \* \* \* \*